United States Patent
Shi et al.

(10) Patent No.: US 10,591,985 B2
(45) Date of Patent: *Mar. 17, 2020

(54) METHOD AND DEVICE FOR DETERMINING ACTION AND/OR ACTION PART

(71) Applicant: BEIJING ZHIGU RUI TUO TECH CO., LTD., Beijing (CN)

(72) Inventors: Yuanchun Shi, Beijing (CN); Yuntao Wang, Beijing (CN); Chun Yu, Beijing (CN); Lin Du, Beijing (CN)

(73) Assignee: BEIJING ZHIGU RUI TUO TECH CO., LTD., Beijing (CN)

( * ) Notice: Subject to any disclaimer, the term of this patent is extended or adjusted under 35 U.S.C. 154(b) by 118 days.

This patent is subject to a terminal disclaimer.

(21) Appl. No.: 15/548,721

(22) PCT Filed: Jan. 7, 2016

(86) PCT No.: PCT/CN2016/070402
§ 371 (c)(1),
(2) Date: Aug. 3, 2017

(87) PCT Pub. No.: WO2016/127745
PCT Pub. Date: Aug. 18, 2016

(65) Prior Publication Data
US 2018/0018016 A1    Jan. 18, 2018

(30) Foreign Application Priority Data
Feb. 10, 2015  (CN) .......................... 2015 1 0069988

(51) Int. Cl.
*G06F 3/01* (2006.01)
*A61B 5/026* (2006.01)
*A61B 8/06* (2006.01)
*A61B 8/08* (2006.01)
*A61B 5/00* (2006.01)
(Continued)

(52) U.S. Cl.
CPC ............ *G06F 3/011* (2013.01); *A61B 5/0261* (2013.01); *A61B 5/6826* (2013.01); *A61B 8/06* (2013.01);
(Continued)

(58) Field of Classification Search
CPC .......... G06F 3/011; G06F 3/017; G06F 1/163; A61B 5/0261; A61B 5/6826; A61B 8/06;
(Continued)

(56) References Cited

U.S. PATENT DOCUMENTS 8,808,179 B1 *  8/2014  Cinberg ................. A61B 3/113
                                                            600/300
10,261,577 B2 *  4/2019  Shi .......................... G06F 3/011
(Continued)

FOREIGN PATENT DOCUMENTS

CN            1947085 A        4/2007
CN          103941874 A        7/2014
(Continued)

OTHER PUBLICATIONS

International Search Report and Written Opinion for Application No. PCT/CN2016/070402, dated Apr. 2, 2016, 10 pages.
(Continued)

*Primary Examiner* — Stephen G Sherman
(74) *Attorney, Agent, or Firm* — Sheppard Mullin Richter & Hampton LLP

(57) ABSTRACT

The present application provides methods and devices for determining an action and/or an action part, and generally relates to the field of wearable devices. A method disclosed herein comprises: in response to that a first part on a body of a user executes an action, acquiring target blood flow information of the first part or a second part corresponding to the first part; and determining the first part and/or the action according to the target blood flow information and
(Continued)

reference information. The methods and devices provide a new scheme for recognizing an action and/or an action part.

26 Claims, 12 Drawing Sheets

(51) Int. Cl.
*G06F 1/16* (2006.01)
*G06K 9/00* (2006.01)

(52) U.S. Cl.
CPC .............. *A61B 8/488* (2013.01); *G06F 1/163* (2013.01); *A61B 8/5223* (2013.01); *A61B 2503/12* (2013.01); *G06F 3/017* (2013.01); *G06K 9/0053* (2013.01); *G06K 9/00355* (2013.01); *G06K 9/00543* (2013.01)

(58) Field of Classification Search
CPC ... A61B 8/488; A61B 8/5223; A61B 2503/12; G06K 9/00355; G06K 9/0053; G06K 9/00543

See application file for complete search history.

(56) References Cited

U.S. PATENT DOCUMENTS

| | | | | |
|---|---|---|---|---|
| 2007/0016045 A1* | 1/2007 | Zhang | ..................... | A61B 8/06 600/443 |
| 2007/0164201 A1* | 7/2007 | Liess | .................. | G06F 3/03547 250/221 |
| 2009/0143688 A1 | 6/2009 | Rekimoto | | |
| 2014/0121528 A1 | 5/2014 | Rekimoto | | |
| 2014/0257050 A1 | 9/2014 | Kuroda et al. | | |
| 2016/0332025 A1* | 11/2016 | Repka | ................ | A63B 24/0062 |
| 2017/0147079 A1 | 5/2017 | Shi et al. | | |

FOREIGN PATENT DOCUMENTS

| | | | |
|---|---|---|---|
| CN | 104027103 | A | 9/2014 |
| CN | 104049752 | A | 9/2014 |
| CN | 104656895 | A | 5/2015 |
| CN | 104656896 | A | 5/2015 |
| CN | 104699241 | A | 6/2015 |
| CN | 104699242 | A | 6/2015 |

OTHER PUBLICATIONS

Morganti, E. et al., "A smart watch with embedded sensors to recognize objects, grasps and forearm gestures," International Symposium on Robotics and Intelligent Sensors, Procedia Engineering, 2012, vol. 41, p. 1169-1175.

Yousefi, R. et al., "Adaptive Cancellation of Motion Artifact in Wearable Biosensors," 34th Annual International Conference of the IEEE EMBS, Sep. 2012, p. 2004-2008.

* cited by examiner

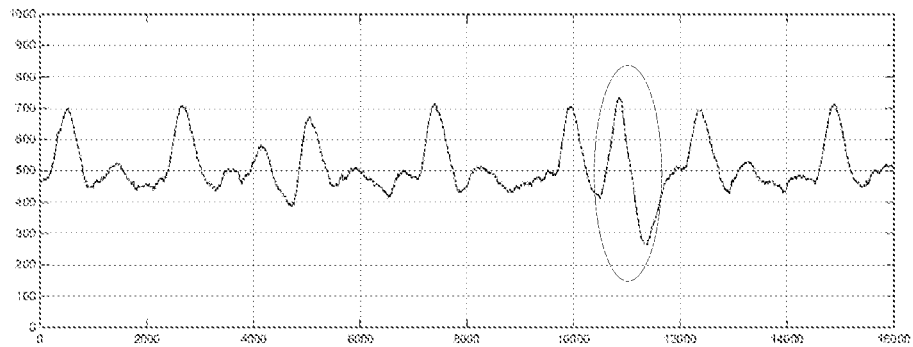
FIG. 9
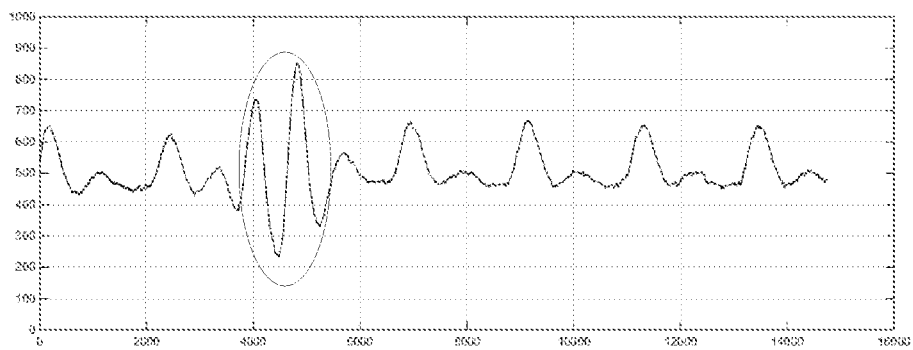
FIG. 10
Compute similarity between a waveform of the target difference information and at least one known waveform, and determine a target known waveform according to a computation result — S1421a
Determine the first part and/or the action according to the target known waveform — S1422a
FIG. 11

METHOD AND DEVICE FOR DETERMINING ACTION AND/OR ACTION PART

CROSS-REFERENCE TO RELATED APPLICATION

The application is a National Phase Application of International Application No. PCT/CN2016/070402, filed on Jan. 7, 2016, which claims priority to and benefit of Chinese Patent Application No. 201510069988.1, filed on Feb. 10, 2015, and entitled "Method and Device for Determining Action and/or Action Part". Both of the above-referenced applications are incorporated into the present application by reference herein in their entirety.

RELATED APPLICATION

The present international patent cooperative treaty (PCT) application claims priority to and benefit of Chinese Patent Application No. 201510069988.1, filed on Feb. 10, 2015, and entitled "Method and Device for Determining Action and/or Action Part", which is hereby incorporated into the present international PCT application by reference herein in its entirety.

TECHNICAL FIELD

The present application relates to the field of wearable devices, and in particular, to methods and device for determining an action and/or an action part.

BACKGROUND

With popularization and development of electronic devices, present electronic devices are more and more intelligent, and recognition by the electronic devices of user actions is one of intelligent development directions thereof.

For example, some gaming devices can recognize users' simple gesture actions through an image recognition technology; some smart bracelets and other wearable devices can recognize whether a user is currently walking through an acceleration sensor, and can implement a step recording function.

SUMMARY

An objective of the present application is to provide a method and device for determining an action and/or an action part.

According to one aspect, at least one embodiment of the present application provides a method for determining an action and/or an action part, the method comprising:

in response to that a first part on a body of a user executes an action, acquiring target Doppler measurement information of the first part or a second part corresponding to the first part; and determining the first part and/or the action according to the target Doppler measurement information and reference information.

According to one aspect, at least one embodiment of the present application provides a device for determining an action and/or an action part, the device comprising:

an acquisition module, configured to, in response to that a first part on a body of a user executes an action, acquire target Doppler measurement information of the first part or a second part corresponding to the first part; and a first determination module, configured to determine the first part and/or the action according to the target Doppler measurement information and reference information.

According to one aspect, at least one embodiment of the present application provides a method for determining an action and/or an action part, the method comprising:

in response to that a first part on a body of a user executes an action, acquiring target blood flow information of the first part or a second part corresponding to the first part; and determining the first part and/or the action according to the target blood flow information and reference information.

According to one aspect, at least one embodiment of the present application provides a device for determining an action and/or an action part, the device comprising:

an acquisition module, configured to, in response to that a first part on a body of a user executes an action, acquire target blood flow information of the first part or a second part corresponding to the first part; and a first determination module, configured to determine the first part and/or the action according to the target blood flow information and reference information.

The method and device for determining an action and/or an action part according to the embodiments of the present application, in response to that a first part on a body of a user executes an action, acquire target blood flow information of the first part or a second part corresponding to the first part, and determine the first part and/or the action according to the target blood flow information and reference information, so as to provide a new scheme for recognizing an action and/or an action part.

BRIEF DESCRIPTION OF THE DRAWINGS

FIG. 9 is a schematic diagram of target PPG information obtained in the event of a single click by an index finger in one implementation of the present application;

FIG. 10 is a schematic diagram of target PPG information obtained in the event of a double click by an index finger in one implementation of the present application;

FIG. 11 is a detailed flowchart of step S142a in one implementation of the present application;

DETAILED DESCRIPTION

Specific implementations of the present application are further described in detail hereinafter with reference to the accompanying drawings and embodiments. The following embodiments are intended to describe the present application, but not to limit the scope of the present application.

It should be understood by those skilled in the art that, in the embodiments of the present application, the value of the serial number of each step described below does not mean an execution sequence, and the execution sequence of each step should be determined according to the function and internal logic thereof, and should not be any limitation to the implementation procedure of the embodiments of the present application.

In a research process, the inventor has found that if a body of a user is in a motion state, it will result in that collected blood flow information comprises noise produced by the motion. Generally, people will consider how to eliminate the noise, so as to increase accuracy of the collected blood flow information.

The inventor has also found that motion of different parts of the body of the user or different motion of the same part may result in production of different noise, and then result in that the collected blood flow information has different waveform features. On this basis, which part performs which action can be reasonably inferred according to the obtained blood flow information, so as to achieve recognition of an action and/or an action part. The blood flow information may be PPG (photoplethysmography) information or may be Doppler measurement information.

Figure 1:
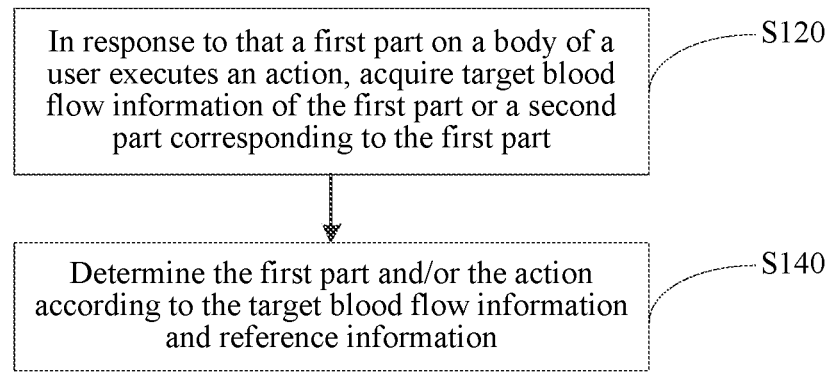
FIG. 1 is a flowchart of a method for determining an action and/or an action part according to one embodiment of the present application.

FIG. 1 is a flowchart of a method for determining an action and/or an action part according to one embodiment of the present application; the method may be, for example, implemented on a device for determining an action and/or an action part. As shown in FIG. 1, the method comprises:

S120: in response to that a first part on a body of a user executes an action, acquiring target blood flow information of the first part or a second part corresponding to the first part; and S140: determining the first part and/or the action according to the target blood flow information and reference information.

The method according to one embodiment of the present application, in response to that a first part on a body of a user executes an action, acquires target blood flow information of the first part or a second part corresponding to the first part, and determines the first part and/or the action according to the target blood flow information and reference information, so as to provide a new scheme for recognizing an action and/or an action part.

Functions of steps S120 and S140 are described below in detail in combination with specific implementations.

S120: In response to that a first part on a body of a user executes an action, acquire target blood flow information of the first part or a second part corresponding to the first part.

The first part, that is, the action part, for example, may be the user's finger, palm, wrist, neck, foot, leg and the like. The first part, in addition to serving as an action part, may also serve as an acquisition part of target blood flow information, for example, in the event that an acquisition sensor of target blood flow information is a smart bracelet, the wrist may serve as an action part and an acquisition part at the same time.

The second part is another optional acquisition part of target blood flow information, and the second part is a part adjacent to the first part, in other words, a distance between the first part and the second part should be less than a distance threshold, for example, less than 0.1 m. Moreover, the inventor has found in a research process that the smaller the distance between the first part and the second part is, the smaller the error of the method is. Generally, the first part and the second part are located on the same limb of the user. For example, in the event that a finger serves as an action part, the wrist on the same limb may serve as an acquisition part.

For the sake of clarity, in the following, the part in the first part and the second part which actually acquires the target blood flow information is called the acquisition part of the target blood flow information.

The action may be some daily common actions, for example, a finger clicks, a palm makes a fist, a palm is open and the like, and may also be some training actions, for example, a finger quickly double clicks and the like.

As stated above, the blood flow information may be PPG information or Doppler measurement information, and correspondingly, the target blood flow information may be target Doppler measurement information of target Doppler measurement information.

Figure 2:
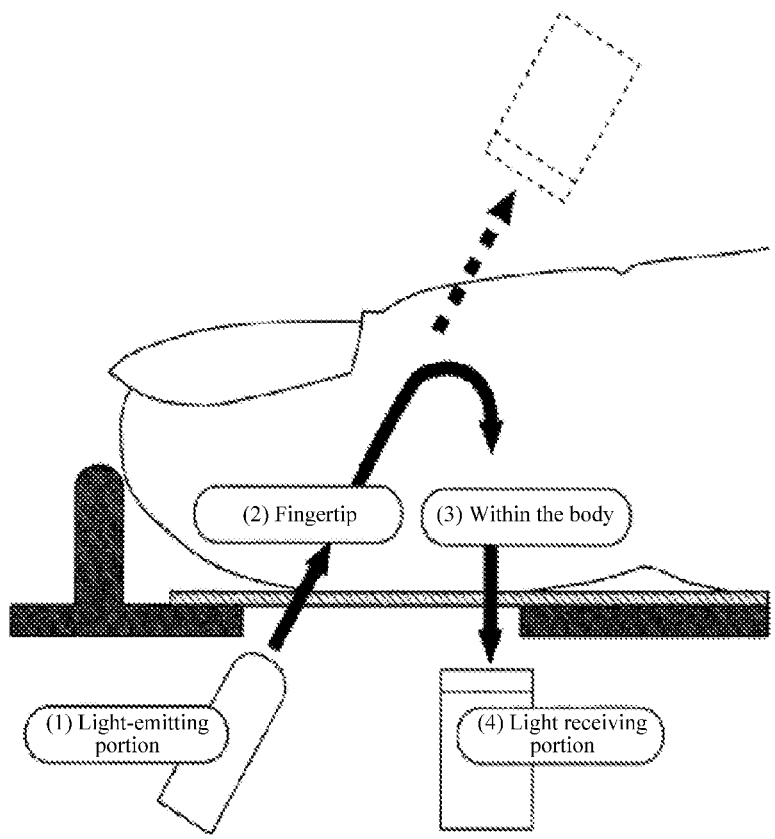
FIG. 2 is a schematic diagram of detecting PPG information in one implementation of the present application.
Figure 3:
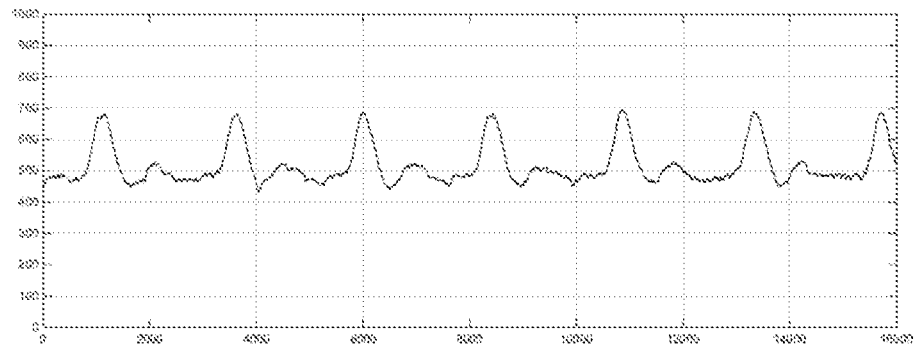
FIG. 3 is a schematic diagram of PPG information detected normally.

FIG. 2 is a schematic diagram of acquisition of human body PPG information. Its principle is that, after light emitted by a light-emitting portion is reflected by a fingertip, a light receiving portion detects intensity of the reflected light. As blood may have an absorption effect on light, the intensity of the reflected light will vary with changes of quantity of blood flow flowing through the fingertip in one unit of time. PPG information can be obtained by measuring a cycle of changes of the reflected light, and then heart rate and other information can be computed. As hemoglobin in the blood has the best absorption effect on green light, a green light LED can generally be used as a light-emitting portion. Under normal circumstances, an oscillogram of PPG information as shown in FIG. 3 can be detected.

Figure 4:
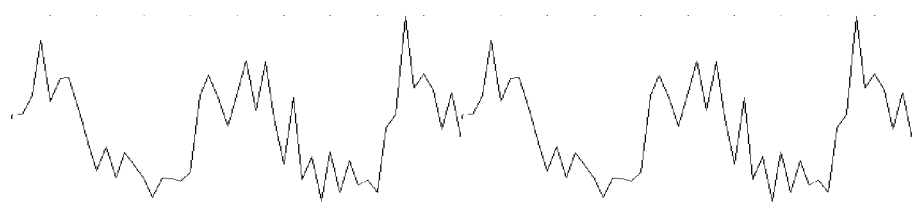
FIG. 4 is a schematic diagram of LDF information detected normally.

The principle of acquiring LDF information is that a laser signal emitted by a light-emitting unit, after being reflected by red blood cells, is detected by a photoelectric sensor, and a flow velocity of the blood and the size of the blood flow can be measured by analyzing Doppler shift of electrical signals output by the photoelectric sensor. An optical blood flow sensor based on an LDF principle can be configured to measure a heart rate and the like. Under normal circumstances, an oscillogram of LDF information as shown in FIG. 4 can be detected.

S140: Determine the first part and/or the action according to the target blood flow information and reference information.

a) In one implementation, the target blood flow information is target Doppler measurement information, and correspondingly, step S140 further comprises:

S140a: determining the first part and/or the action according to the target Doppler measurement information and reference information.

In the event that the target PPG information accurately corresponds to the action, the first part and/or the action can be determined more accurately according to the target PPG information and the reference information. However, under some circumstances, the target PPG information may acquire some redundant information excessively, for example, it may comprise some information before or after execution of the action. In this case, determining the first part and/or the action directly according to the target PPG information and the reference information may lead to a lower accuracy rate of recognition.

Figure 5:
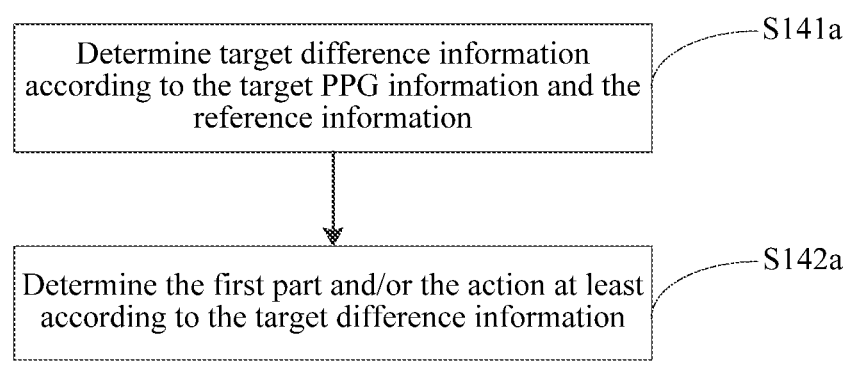
FIG. 5 is a detailed flowchart of step S140a in one implementation of the present application.

Therefore, referring to FIG. 5, in one implementation, step S140a may further comprise:

S141a: determining target difference information according to the target PPG information and the reference information; and S142a: determining the first part and/or the action at least according to the target difference information.

In one implementation, in step S141a, the reference information may be a first threshold, and the first threshold may be set according to PPG information acquired by the acquisition part in the event that the first part does not execute an action, that is, remains still (hereinafter referred to as PPG information acquired normally), for example, the first threshold is set as a minimum amplitude value of the PPG information acquired normally, or set as a maximum amplitude value of the PPG information acquired normally.

Figure 6:
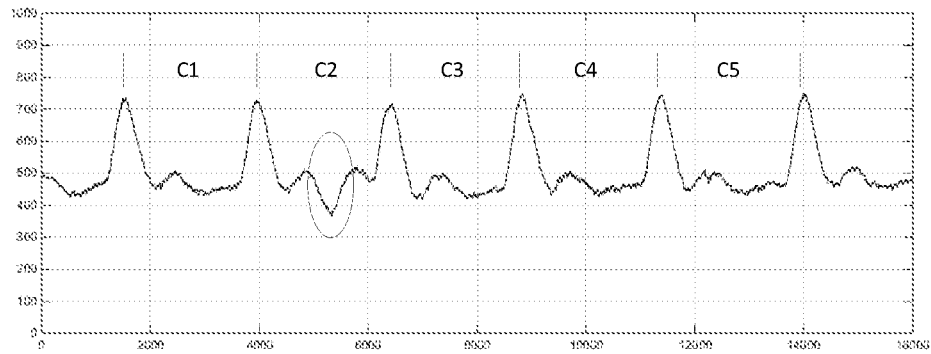
FIG. 6 is a schematic diagram of PPG information detected in the event of a single click by a middle finger in one implementation of the present application.

The target difference information is partial information in the target PPG information, and the action results in that the partial information is evidently distinguished from the PPG information acquired normally. For example, in the event of a single click by a middle finger, a waveform of the target PPG information obtained is as shown in FIG. 6, part of the waveform within a circle is evidently distinguished from the waveform outside the circle. The part within the circle is a waveform corresponding to the target difference information, which is the waveform obtained according to changes of a normal PPG waveform caused by the single click by the middle finger. It can be seen that the minimum amplitude value of the part of the waveform within the circle is evidently lower than the amplitude value of the PPG information acquired normally.

Therefore, in one implementation, step S141a is further:

S14a': comparing an amplitude value in the target Doppler measurement information with a value of the reference information, and determining the target difference information according to a comparison result.

Specifically, in the event that the reference information is the minimum amplitude value of the PPG information acquired normally, it is feasible to determine a part in the target PPG information whose amplitude value is less than the value of the reference information as the target difference information. Certainly, in the event that the reference information is the maximum amplitude value of the PPG information acquired normally, it is feasible to determine a part in the target PPG information whose amplitude value is greater than the value of the reference information as the target difference information. By taking FIG. 7 as an example, which shows a waveform of the target PPG information obtained at a wrist in the event of making a fist, part of the waveform within a solid circle is evidently distinguished from the waveform outside the solid circle. The part of the waveform within the solid circle is a waveform corresponding to the target difference information, which is the waveform obtained according to changes of a normal PPG waveform caused by making a fist. It can be seen that the maximum amplitude value of the part of the waveform within the solid circle is evidently higher than the amplitude value of the PPG information acquired normally.

Figure 7:
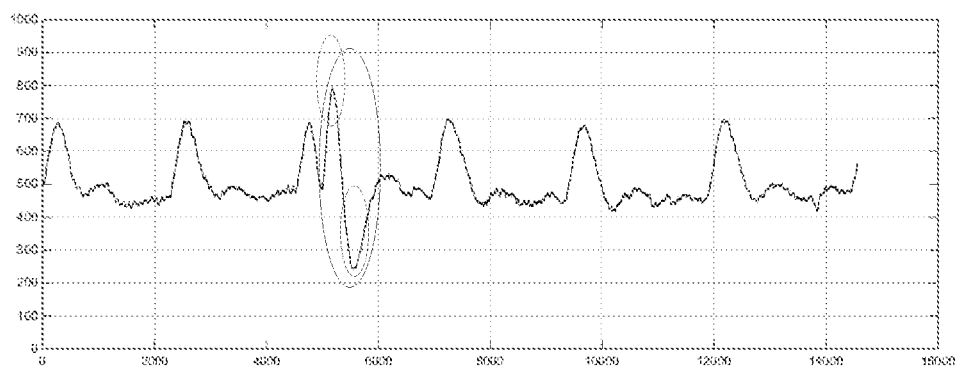
FIG. 7 is a schematic diagram of PPG information detected in the event of making a fist in one implementation of the present application.

Those skilled in the art should understand that, for the target Doppler measurement information in FIG. 7, the target difference information obtained according to the processing in step S141a' may be merely waveforms in two dotted circles, that is, an overall waveform within the solid circle may not be obtained, however, the number of times the action is executed can be inferred according to the waveforms in the two dotted circles, and in combination with, for example, time and other information, which may assist with recognition of the action and the action part.

In another implementation, in step S141a, the reference information may be reference PPG information acquired at the first part or the second part in the event that the first part does not execute an action, that is, PPG information acquired normally. A waveform of the reference PPG information may be as shown in FIG. 3, which can be pre-acquired.

Figure 8:
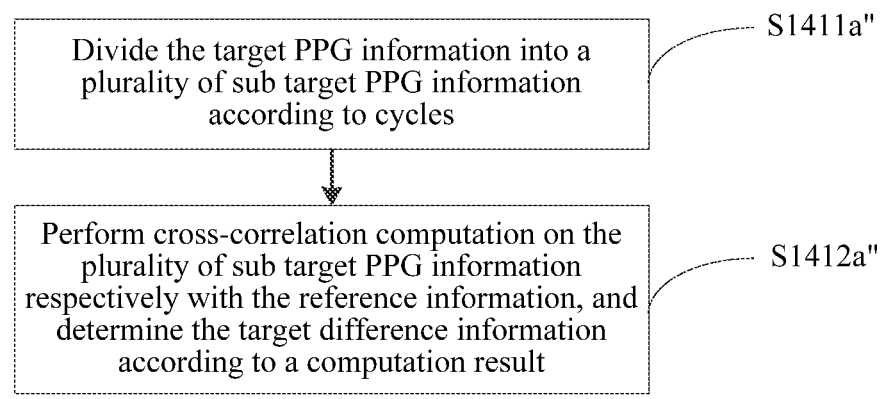
FIG. 8 is a detailed flowchart of step S141a in one implementation of the present application.

Correspondingly, referring to FIG. 8, in one implementation, step S141a may comprise:

S1411a'': dividing the target PPG information into a plurality of sub target PPG information according to cycles; and S1412a'': performing cross-correlation computation on the plurality of sub target PPG information respectively with the reference information, and determining the target difference information according to a computation result.

Still by taking the waveform shown in FIG. 6 as an example, in step S1411a'', it is feasible to divide the waveform shown in FIG. 6 into C1, C2, C3, C4 and C5 according to one cycle between adjacent crests, there are a total of 5 sub-waveforms, and the 5 sub-waveforms correspond to 5 sub target Doppler measurement information. Waveforms at edge portions can be omitted, because some PPG information may be acquired excessively in acquisition of the target PPG information.

In step S1412a'', the reference information may be a PPG waveform between two crests acquired normally, after cross-correlation computation is performed on the reference information with the 5 sub target PPG information respectively, it can be found that a cross-correlation computation result between the reference information and C2 is evidently less than that between the reference information and other sub target PPG information, and it can be determined accordingly that PPG information corresponding to C2 is the target difference information.

In actual applications, it is feasible to compare the cross-correlation computation result between the reference information and each sub target PPG information with a threshold, if the result is less than the threshold, it is considered that the corresponding sub target PPG information is the target difference information. The threshold may be, for example, set as 80% of a cross-correlation computation result between the reference information and itself.

Those skilled in the art should understand that the two manners of determining the target difference information may also be used in combination, so as to increase accuracy and efficiency.

In one implementation, step S142a may further comprise:

S142a': determining the action according to the number of troughs or crests comprised in the target difference information.

The number of troughs or crests comprised in the target difference information is the same as the number of times the action is executed. As shown in FIG. 6, in the event of a single click action of a middle finger, the number of the corresponding troughs is 1; as shown in FIG. 7, in the event of a single fist making, the number of the corresponding troughs or crests is 1. In addition, FIG. 9 is a waveform of target PPG information obtained in the event of a single click by an index finger, a waveform within a circle corresponds to the target difference information, and the number of the troughs or crests corresponding thereto is also 1; FIG. 10 is a waveform of target PPG information obtained in the event of a double click by an index finger, a waveform within a circle corresponds to the target difference information, and it can be seen that, in this case, the number of the troughs or crests comprised in the target difference information is 2.

In another implementation, step S142a may further comprise:

S142a'': determining the action according to a cycle corresponding to the target difference information.

The cycle corresponding to the target difference information corresponds to a cycle within which the first part executes the action, in other words, the longer the time the first part executes the action each time is, the longer the cycle of the target difference information is. Therefore, the cycle corresponding to the target difference information may reflect a speed at which the action is executed, and then the action can be determined. For example, the first part is a foot, and if the cycle within which the foot executes a raise and lower action is 0.3 s, it can be determined that the corresponding action is walking; if the cycle within which the foot executes a raise and lower action is 0.03 s, it can be determined that the corresponding action is running. Certainly, in the event that the first part is a hand, whether the user is walking or running may also be determined according to a cycle of swinging back and forth of the hand.

In another implementation, referring to FIG. 11, step S142a may further comprise:

S1421a: computing similarity between a waveform of the target difference information and at least one known waveform, and determining a target known waveform according to a computation result; and S1422a: determining the first part and/or the action according to the target known waveform.

The at least one known waveform may be a set of multiple known waveforms, which can be obtained through pre-training, for example, a user orders the first part to execute different actions in advance and correspondingly acquire a waveform of the corresponding target difference information as the known waveform. So, a corresponding relationship between the first part, the action and the known waveform can be established, and the corresponding relationship can be as shown in Table 1.

TABLE 1

| First part | Action | Known waveform |
| --- | --- | --- |
| Index finger | Single click | A |
| Index finger | Double click | B |
| Middle finger | Single click | C |
| Hand | Make a fist | D |
| Hand | Open | E |

In actual applications, similarity between the waveform of the target difference information acquired in step S1421a and each known waveform in the set may be computed, and then a known waveform with the highest similarity is selected as the target known waveform. Then, in step S1422a, the first part and/or the action can be determined according to the target known waveform.

By taking the first line in Table 1 as an example, suppose that the waveform of the target difference information is as shown by the waveform within the circle in FIG. 9, it can be obtained after computation that the similarity between the waveform of the target difference information and the known waveform A is the highest, the target known waveform can be determined as the known waveform A, and then it can be determined that the first part is an index finger and the action is single click.

Figure 12:
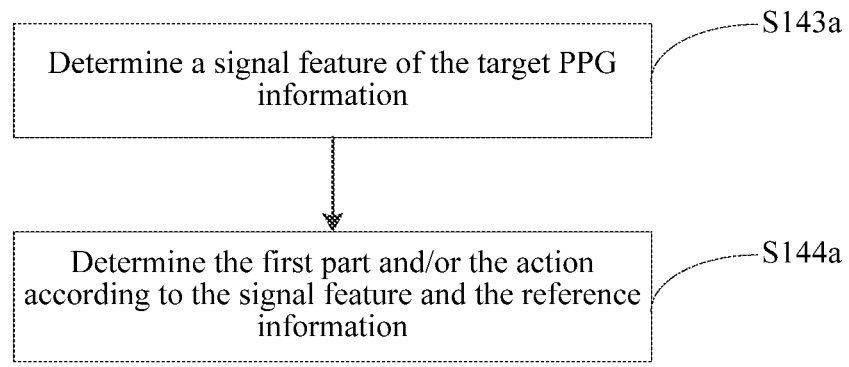
FIG. 12 is a detailed flowchart of step S140a in one implementation of the present application.

In addition, referring to FIG. 12, in another implementation, step S140a may comprise:

S143a: determining a signal feature of the target PPG information; and

S144a: determining the first part and/or the action according to the signal feature and the reference information.

In step S143a, the signal feature of the target PPG information comprises at least one of a fingerprint, an average value and a difference of the target PPG information; the fingerprint consists of at least one of amplitude, phase and frequency spectrum of the target PPG information; the average value is an average value of at least one of the amplitude, the phase and the frequency spectrum of the target PPG information; the difference is a difference of at least one of the amplitude, the phase and the frequency spectrum of the target PPG information.

In step S144a, the reference information may be a reference signal feature obtained through pre-training, for example, in a training stage, it is feasible to execute a corresponding action according to Table 1 and correspondingly acquire a signal feature of the corresponding PPG information as the reference information. In specific applications, similarity between the signal feature of the target PPG information and a plurality of reference information can be computed, and a part and/or an action corresponding to the reference information with the highest similarity is taken as the first part and/or the action.

b) In another implementation, the target blood flow information is target Doppler measurement information, and correspondingly, step S140 may further comprise:

S140b: determining the first part and/or the action according to the target Doppler measurement information and reference information.

The target Doppler measurement information may be, for example, LDF (Laser Doppler Flowmetry), LDV (Laser Doppler Velocimety), ultrasonic Doppler shift and the like.

Figure 13:
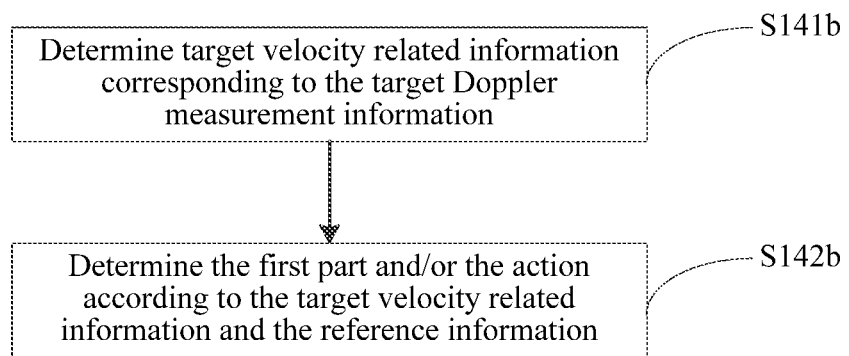
FIG. 13 is a detailed flowchart of step S140b in one implementation of the present application.

Referring to FIG. 13, in one implementation, step S140b may comprise:

S141b: determining target velocity related information corresponding to the target Doppler measurement information; and S142b: determining the first part and/or the action according to the target velocity related information and the reference information.

As stated above, the target Doppler measurement information may be, for example, LDF, LDV, ultrasonic Doppler shift and the like, which comprises a series of envelope wave signals, corresponding frequency-domain signals can be obtained by performing, for example, fast Fourier transform thereon, Doppler frequency components in the frequency-domain signals are in direct proportion to a blood flow velocity, a velocity of blood flow can be obtained, and blood flow can be determined further according to the blood flow velocity and the number of blood cells comprised in a blood cross section.

The data type of the target velocity related information may be the blood flow velocity, and may also be the blood flow. In other words, the target velocity related information may be target blood flow velocity information or target blood flow information. As the target Doppler measurement information comprises noise caused by the action, the target velocity related information also comprises the noise. Specifically, the noise comprises a change of the blood flow velocity caused by motion and/or a detection error caused by a change of contact between a detection device of the target Doppler measurement information and a limb (different actions will cause different changes of the contact between the detection device and the limb). In an ordinary LDF detection process, people generally tend to avoid such noise, but the present application achieves recognition of the action by use of such noise.

In one implementation, step S142b may further comprise:

S1421b: determining target difference information according to the target velocity related information and the reference information; and S1422b: determining the first part and/or the action at least according to the target difference information.

Figure 14:
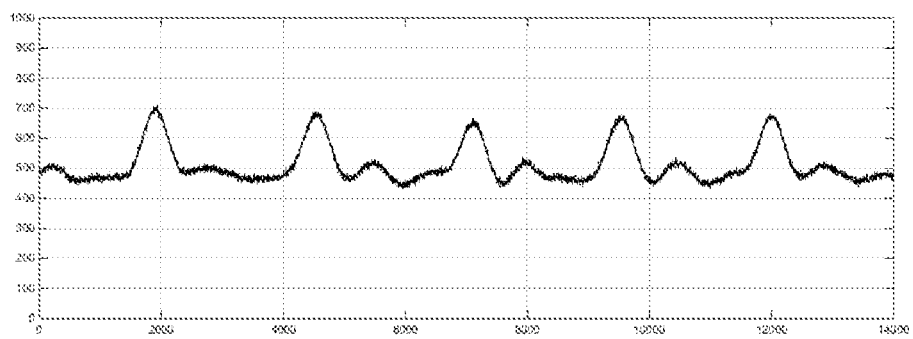
FIG. 14 is a schematic diagram of reference velocity related information in one implementation of the present application.

In step S1421b, the reference information may be of different types. For example, in one implementation, the reference information is reference velocity related information corresponding to reference Doppler measurement information acquired by an acquisition part of the target Doppler measurement information in the event that the first part does not execute the action. Similar to the target velocity related information, the reference velocity related information may also be blood flow velocity or blood flow. In the event that the reference velocity related information is blood flow, a waveform thereof may be as shown in FIG. 14, it can be seen that it has an evident periodic regularity, and heart rate, pulse and other information can be obtained according to the waveform.

Correspondingly, step S1421b may further comprise:

S14211b: dividing the target velocity related information into a plurality of sub target velocity related information according to cycles; and S14212b: performing cross-correlation computation on the plurality of sub target velocity related information respectively with the reference information, and determining the target difference information according to a computation result.

Figure 15:
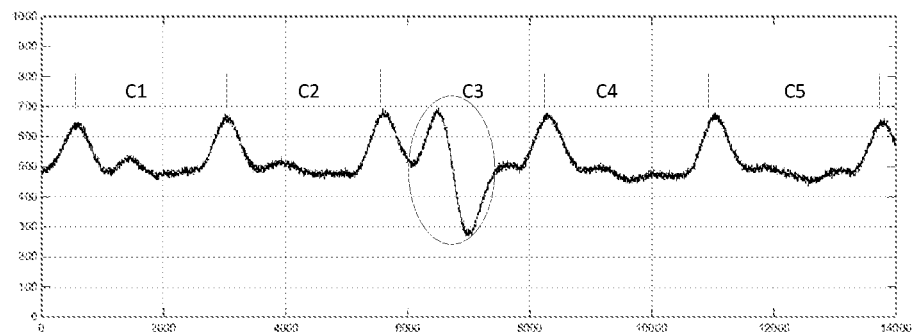
FIG. 15 is a schematic diagram of target velocity related information detected in the event of a single click by an index finger in one implementation of the present application.

In step S14211b, in the event that an index finger executes a single click action, the waveform of the target velocity related information obtained is as shown in FIG. 15, and a total of 5 sub target velocity related information, C1, C2, C3, C4, and C5, can be obtained based on cycle division. The cycles are the same as those of the reference velocity related information.

In step S14212b, the reference information may be, for example, a waveform between two crests in FIG. 14, after cross-correlation computation is performed on the reference information respectively with the 5 sub target velocity related information, it can be found that a cross-correlation computation result between the reference information and C3 is evidently less than that between the reference information and other sub target velocity related information, and it can be determined accordingly that sub target velocity related information corresponding to C3 is the target difference information.

In actual applications, it is feasible to compare the cross-correlation computation result between the reference information and each sub target velocity related information with a threshold, if the result is less than the threshold, it is considered that the corresponding sub target velocity related information is the target difference information. The threshold may be, for example, set as 80% of a cross-correlation computation result between the reference information and itself.

In another implementation, the reference information may be a first threshold, and the first threshold may be set according to an amplitude value of the reference velocity related information, for example, it is set as the minimum amplitude value or the maximum amplitude value of the reference velocity related information.

Correspondingly, step S1421b may further be:

S1421b': comparing an amplitude value in the target velocity related information with a value of the reference information, and determining the target difference information according to a comparison result.

Figure 16:
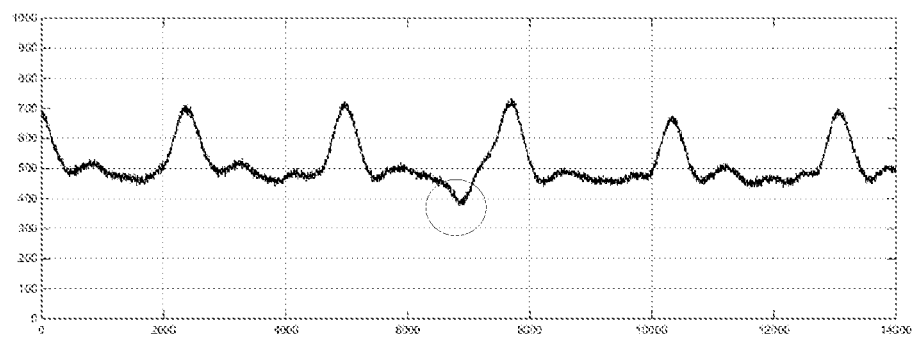
FIG. 16 is a schematic diagram of target velocity related information detected in the event of a single click by a middle finger in one implementation of the present application.

By taking FIG. 16 as an example, which shows a waveform of the target velocity related information obtained in the event that the user's middle finger executes a single click action, the waveform within the circle is evidently distinguished from the waveform outside the circle, and the waveform within the circle is the waveform affected by the single click action, that is, the waveform corresponding to the target difference information. The reference information, for example, may be set as the minimum amplitude value of the reference velocity related information, for example, set as 450, then the amplitude value in the target velocity related information is compared with the amplitude value, it can be seen that the amplitude value of the waveform within the circle is less than the value of the reference information, and it can be determined that the target difference information is the waveform within the circle.

Those skilled in the art should understand that the two manners of determining the target difference information may also be used in combination, so as to increase accuracy and efficiency.

In step S1422b, the first part and/or the action is determined at least according to the target difference information. In one implementation, the step may comprise:

S14221b: computing similarity between a waveform of the target difference information and at least one known waveform, and determining a target known waveform according to a computation result; and S14222b: determining the first part and/or the action according to the target known waveform.

The at least one known waveform may be a set of multiple known waveforms, which can be obtained through pre-training, for example, a user orders the first part to execute different actions in advance and correspondingly acquire a waveform of the corresponding target difference information as the known waveform. So, a corresponding relationship between the first part, the action and the known waveform can be established, and the corresponding relationship can be as shown in Table 1.

In actual applications, in step S14221b, similarity between the waveform of the target difference information and each known waveform in the set may be computed, and then a known waveform with the highest similarity is selected as the target known waveform. Then, in step S14222b, the first part and/or the action can be determined according to the target known waveform.

By taking the first line in Table 1 as an example, suppose that the waveform of the target difference information is as shown by the waveform within the circle in FIG. 15, it can be obtained after computation that the similarity between the waveform of the target difference information and the known waveform A is the highest, the target known waveform can be determined as the known waveform A, and then it can be determined that the first part is an index finger and the action is single click.

In another implementation, step S1422b may further be:

S1422b': determining the action according to the number of troughs or crests comprised in the target difference information.

Figure 17:
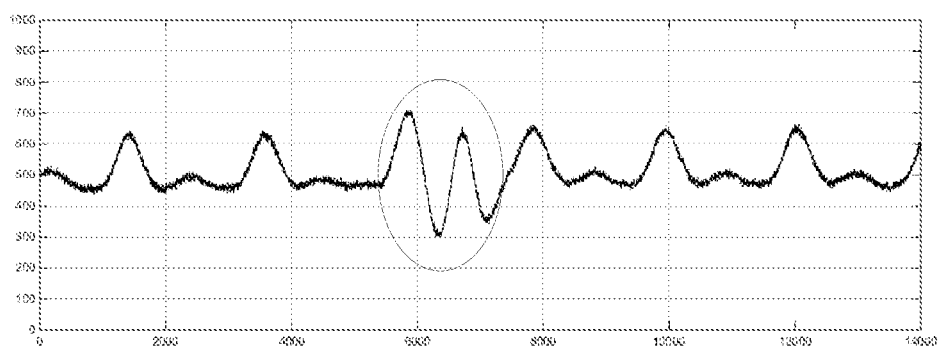
FIG. 17 is a schematic diagram of target velocity related information detected in the event of a double click by an index finger in one implementation of the present application.

The number of troughs or crests comprised in the target difference information is the same as the number of times the action is executed. As shown in FIG. 16, in the event of a single click action of a middle finger, the number of the corresponding troughs is 1; as shown in FIG. 15, in the event of a single click by an index finger, the number of the corresponding troughs or crests is 1. In addition, FIG. 17 is a waveform of target velocity related information obtained in the event of a double click by an index finger, a waveform within a circle corresponds to the target difference information, and it can be seen that, in this case, the number of the troughs or crests comprised in the target difference information is 2.

In another implementation, step S1422b may further be:

S1422b'': determining the action according to a cycle corresponding to the target difference information.

The cycle corresponding to the target difference information corresponds to a cycle within which the first part executes the action, in other words, the longer the time the first part executes the action each time is, the longer the cycle of the target difference information is. Therefore, the cycle corresponding to the target difference information may reflect a speed at which the action is executed, and then the action can be determined. For example, the first part is a foot, and if the cycle within which the foot executes a raise and lower action is 0.3 s, it can be determined that the corresponding action is walking; if the cycle within which the foot executes a raise and lower action is 0.03 s, it can be determined that the corresponding action is running. Certainly, in the event that the first part is a hand, whether the user is walking or running may also be determined according to a cycle of swinging back and forth of the hand.

Figure 18:
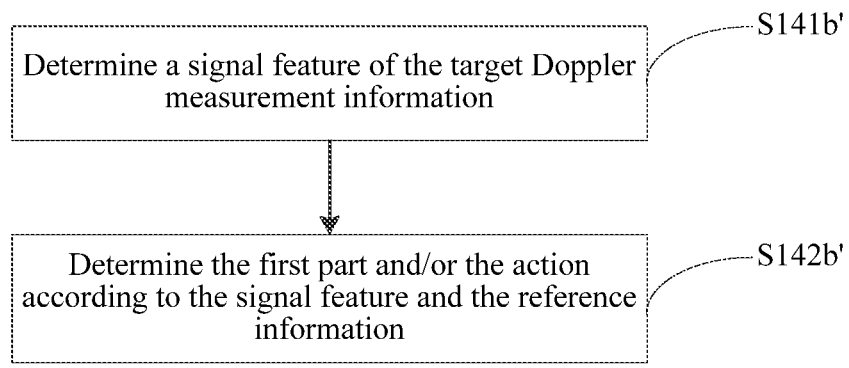
FIG. 18 is a detailed flowchart of step S140b in one implementation of the present application.

In addition, referring to FIG. 18, in another implementation, step S140b may comprise:

S141b': determining a signal feature of the target Doppler measurement information; and S142b': determining the first part and/or the action according to the signal feature and the reference information.

In step S141b', the signal feature of the target Doppler measurement information comprises at least one of a fingerprint, an average value and a difference of the target Doppler measurement information; the fingerprint consists of at least one of amplitude, phase and frequency spectrum of the target Doppler measurement information; the average value is an average value of at least one of the amplitude, the phase and the frequency spectrum of the target Doppler measurement information; the difference is a difference of at least one of the amplitude, the phase and the frequency spectrum of the target Doppler measurement information.

In step S142b', the reference information may be a reference signal feature obtained through pre-training, for example, in a training stage, it is feasible to execute a corresponding action according to Table 1 and correspondingly acquire a signal feature of the corresponding Doppler measurement information as the reference information. In specific applications, similarity between the signal feature of the target Doppler measurement information and a plurality of reference information can be computed, and a part and/or an action corresponding to the reference information with the highest similarity is taken as the first part and/or the action.

Figure 19:
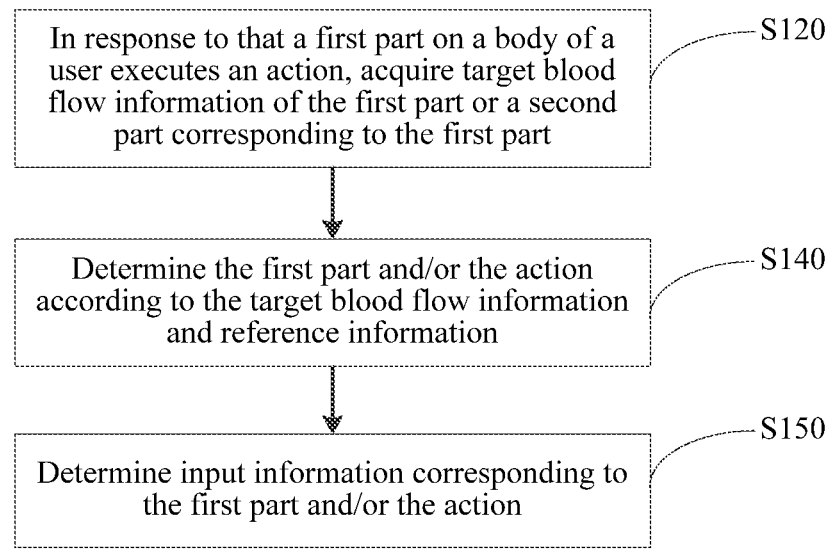
FIG. 19 is a flowchart of a method for determining an action and/or an action part in one implementation of the present application.

In one implementation, referring to FIG. 19, the method further comprises:

S150: determining input information corresponding to the first part and/or the action.

A corresponding relationship between the first part and/or the action and the input information may be pre-determined, and the corresponding relationship may be as shown in Table 2. By taking the second line as an example, suppose that a smart bracelet is in communication with a smart glass, the smart bracelet acquires a user's action instruction and then controls the smart glass, and in the event that the smart bracelet recognizes a double click action of an index finger, the smart bracelet can control the smart glass to open an APP currently presented to the user, for example, open a photograph function. The relationship table shown in Table 2 can be pre-stored in, for example, the smart bracelet and other wearable devices, and such a relationship table can be given in an operation instruction thereof, so as to teach and train the user to execute corresponding command input through an action similar to that in Table 2.

TABLE 2

| First part | Action | Input information |
| --- | --- | --- |
| Index finger | Single click | Selected command |
| Index finger | Double click | Open command |
| Middle finger | Single click | Menu command |
| Hand | Make a fist | Zoom out |
| Hand | Open | Zoom in |

Those skilled in the art should understand that a new scheme based on action and/or action part recognition of the present application can achieve information input by taking a body of a user as an input interface, which facilitates enhancing input capability of, for example, wearable devices.

In addition, an embodiment of the present application further provides a computer readable medium, comprising computer readable instructions that perform the following operations when being executed: performing the operations of steps S120 and S140 of the method in the implementation shown in FIG. 1.

To sum up, the method according to the embodiment of the present application can input information to a corresponding electronic device by taking a body of a user as an input interface, thereby enhancing input capability of wearable devices and the like and enhancing user experience.

Figure 20:
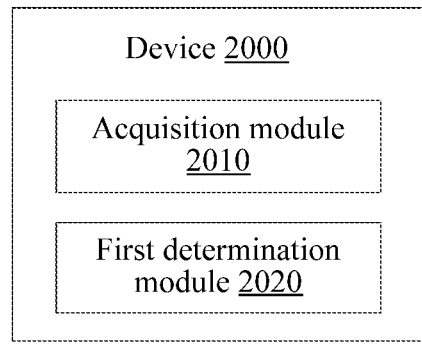
FIG. 20 is a module diagram of a device for determining an action and/or an action part in one implementation of the present application.

FIG. 20 is a schematic diagram of a module structure of a device for determining an action and/or an action part in one implementation of the present application; the device for determining an action and/or an action part may be integrated, as a functional module, into a wearable device such as a smart wristband or a smart watch, and certainly may also be used by the user as a separate wearable device. As shown in FIG. 20, the device 2000 may comprise:

an acquisition module 2010, configured to, in response to that a first part on a body of a user executes an action, acquire target blood flow information of the first part or a second part corresponding to the first part; and a first determination module 2020, configured to determine the first part and/or the action according to the target blood flow information and reference information.

The device according to the embodiment of the present application, in response to that a first part on a body of a user executes an action, acquires target blood flow information of the first part or a second part corresponding to the first part, and determines the first part and/or the action according to the target blood flow information and reference information, so as to provide a new scheme for recognizing an action and/or an action part.

Functions of the acquisition module 2010 and the first determination module 2020 are described below in detail in combination with specific implementations.

The acquisition module 2010, configured to, in response to that a first part on a body of a user executes an action, acquire target blood flow information of the first part or a second part corresponding to the first part.

The first part, that is, the action part, for example, may be the user's finger, palm, wrist, neck, foot, leg and the like. The first part, in addition to serving as an action part, may also serve as an acquisition part of target blood flow information, for example, in the event that an acquisition sensor of target blood flow information is a smart bracelet, the wrist may serve as an action part and an acquisition part at the same time.

The second part is another optional acquisition part of target blood flow information, and the second part is a part adjacent to the first part, in other words, a distance between the first part and the second part should be less than a distance threshold, for example, less than 0.1 m. Moreover, the inventor has found in a research process that the smaller the distance between the first part and the second part is, the smaller the error of the method is. Generally, the first part and the second part are located on the same limb of the user. For example, in the event that a finger serves as an action part, the wrist on the same limb may serve as an acquisition part.

The action may be some daily common actions, for example, a finger clicks, a palm makes a fist, a palm is open and the like, and may also be some training actions, for example, a finger quickly double clicks and the like.

As stated above, the blood flow information may be PPG information or Doppler measurement information, and correspondingly, the target blood flow information may be target Doppler measurement information of target Doppler measurement information.

The first determination module 2020, configured to determine the first part and/or the action according to the target blood flow information and reference information.

a) In one implementation, the target blood flow information is target PPG information, and correspondingly, the first determination module 2020 is configured to determine the first part and/or the action according to the target PPG information and reference information.

In the event that the target PPG information accurately corresponds to the action, the first part and/or the action can be determined more accurately according to the target PPG information and the reference information. However, under some circumstances, the target PPG information may acquire some redundant information excessively, for example, comprise some information before or after execution of the action. In this case, determining the first part and/or the action directly according to the target PPG information and the reference information may lead to a lower accuracy rate of recognition.

Figure 21:
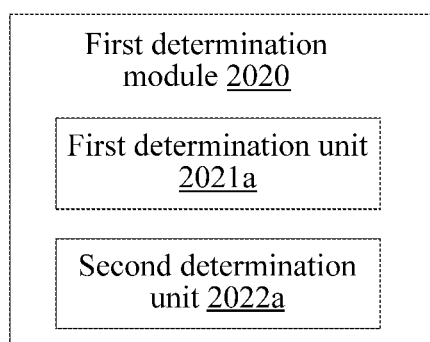
FIG. 21 is a module diagram of the first determination module in one implementation of the present application.

Therefore, referring to FIG. 21, in one implementation, the first determination module 2020 comprises:

a first determination unit 2021a, configured to determine target difference information according to the target PPG information and the reference information; and a second determination unit 2022a, configured to determine the first part and/or the action at least according to the target difference information.

In one implementation, the reference information may be a first threshold, and the first threshold may be set according to PPG information acquired by the acquisition part in the event that the first part does not execute an action, that is, remains still (hereinafter referred to as PPG information acquired normally), for example, the first threshold is set as a minimum amplitude value of the PPG information acquired normally, or set as a maximum amplitude value of the PPG information acquired normally.

The target difference information is partial information in the target Doppler measurement information, and the action results in that the partial information is evidently distinguished from the PPG information acquired normally. For example, in the event of a single click by a middle finger, a waveform of the target PPG information obtained is as shown in FIG. 6, part of the waveform within a circle is evidently distinguished from the waveform outside the circle. The part within the circle is a waveform corresponding to the target difference information, which is the waveform obtained according to changes of a normal PPG waveform caused by the single click by the middle finger. It can be seen that the minimum amplitude value of the part of the waveform within the circle is evidently lower than the amplitude value of the PPG information acquired normally.

Therefore, in one implementation, the first determination unit 2021a is configured to compare an amplitude value in the target PPG information with a value of the reference information, and determine the target difference information according to a comparison result.

Specifically, in the event that the reference information is the minimum amplitude value of the PPG information acquired normally, it is feasible to determine a part in the target PPG information whose amplitude value is less than the value of the reference information as the target difference information. Certainly, in the event that the reference information is the maximum amplitude value of the PPG information acquired normally, it is feasible to determine a part in the target PPG information whose amplitude value is greater than the value of the reference information as the target difference information. By taking FIG. 7 as an example, which shows a waveform of the target PPG information obtained at a wrist in the event of making a fist, part of the waveform within the solid circle is evidently distinguished from the waveform outside the solid circle. The part of the waveform within the solid circle is a waveform corresponding to the target difference information, which is the waveform obtained according to changes of a normal PPG waveform caused by making a fist. It can be seen that the maximum amplitude value of the part of the waveform within the solid circle is evidently higher than the amplitude value of the PPG information acquired normally.

Those skilled in the art should understand that, for the target PPG information in FIG. 7, the target difference information obtained according to the processing in step S141a' may be merely waveforms in the two dotted circles, that is, an overall waveform within the solid circle may not be obtained, however, the number of times the action is executed can be inferred according to the waveforms in the two dotted circles, and in combination with, for example, time and other information, which may assist in recognition of the action and the action part.

In another implementation, the reference information may be reference PPG information acquired at the first part or the second part in the event that the first part does not execute an action, that is, PPG information acquired normally. A waveform of the reference PPG information may be as shown in FIG. 3, which can be pre-acquired.

Figure 22:
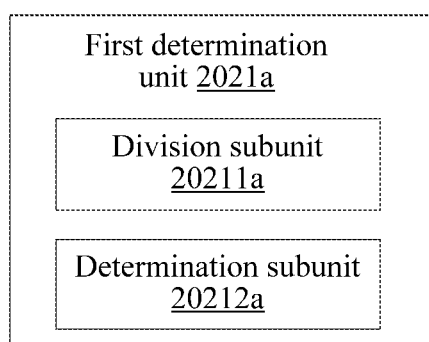
FIG. 22 is a module diagram of the first determination unit in one implementation of the present application.

Correspondingly, referring to FIG. 22, in one implementation, the first determination unit 2021a comprises:

a division subunit 20211a, configured to divide the target PPG information into a plurality of sub target PPG information according to cycles; and a determination subunit 20212a, configured to perform cross-correlation computation on the plurality of sub target PPG information respectively with the reference information, and determine the target difference information according to a computation result.

By taking the waveform shown in FIG. 6 as an example, it is feasible to divide the waveform shown in FIG. 6 into C1, C2, C3, C4, and C5 according to one cycle between adjacent crests, there are a total of 5 sub-waveforms, and the 5 sub-waveforms correspond to 5 sub target PPG information. Waveforms at edge portions can be omitted, because some PPG information may be acquired excessively in acquisition of the target PPG information.

The reference information may be a PPG waveform between two crests acquired normally, after cross-correlation computation is performed on the reference information with the 5 sub target PPG information respectively, it can be found that a cross-correlation computation result between the reference information and C2 is evidently less than that between the reference information and other sub target PPG information, and it can be determined accordingly that PPG information corresponding to C2 is the target difference information.

In actual applications, it is feasible to compare the cross-correlation computation result between the reference information and each sub target PPG information with a threshold, if the result is less than the threshold, it is considered that the corresponding sub target PPG information is the target difference information. The threshold may be, for example, set as 80% of a cross-correlation computation result between the reference information and itself.

Those skilled in the art should understand that the two manners of determining the target difference information may also be used in combination, so as to increase accuracy and efficiency.

In one implementation, the second determination unit 2022a is configured to determine the action according to the number of troughs or crests comprised in the target difference information.

The number of troughs or crests comprised in the target difference information is the same as the number of times the action is executed. As shown in FIG. 6, in the event of a single click action of a middle finger, the number of the corresponding troughs is 1; as shown in FIG. 7, in the event of a single fist, the number of the corresponding troughs or crests is 1. In addition, FIG. 9 is a waveform of target PPG information obtained in the event of a single click by an index finger, a waveform within a circle corresponds to the target difference information, and the number of the troughs or crests corresponding thereto is also 1; FIG. 10 is a waveform of target PPG information obtained in the event of a double click by an index finger, a waveform within a circle corresponds to the target difference information, and it can be seen that, in this case, the number of the troughs or crests comprised in the target difference information is 2.

In another implementation, the second determination unit 2022a is configured to determine the action according to a cycle corresponding to the target difference information.

The cycle corresponding to the target difference information corresponds to a cycle within which the first part executes the action, in other words, the longer the time the first part executes the action each time is, the longer the cycle of the target difference information is. Therefore, the cycle corresponding to the target difference information may reflect a speed at which the action is executed, and then the action can be determined. For example, the first part is a foot, and if the cycle within which the foot executes a raise and lower action is 0.3 s, it can be determined that the corresponding action is walking; if the cycle within which the foot executes a raise and lower action is 0.03 s, it can be determined that the corresponding action is running. Certainly, in the event that the first part is a hand, whether the user is walking or running may also be determined according to a cycle of swinging back and forth of the hand.

Figure 23:
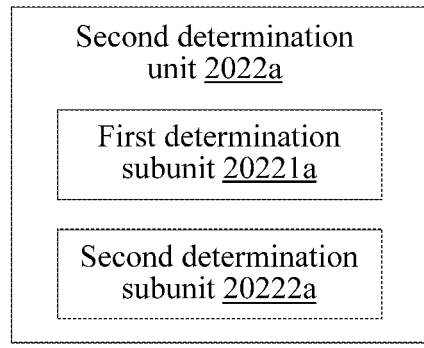
FIG. 23 is a module diagram of the second determination unit in one implementation of the present application.

In another implementation, referring to FIG. 23, the second determination unit 2022a comprises:

a first determination subunit 20221a, configured to compute similarity between a waveform of the target difference information and at least one known waveform, and determine a target known waveform according to a computation result; and a second determination subunit 20222a, configured to determine the first part and/or the action according to the target known waveform.

The at least one known waveform may be a set of multiple known waveforms, which can be obtained through pre-training, for example, a user orders the first part to execute different actions in advance and correspondingly acquire a waveform of the corresponding target difference information as the known waveform. So, a corresponding relationship between the first part, the action and the known waveform can be established, and the corresponding relationship can be as shown in Table 1.

In actual applications, similarity between the waveform of the target difference information and each known waveform in the set may be computed, and then a known waveform with the highest similarity is selected as the target known waveform. Then, the first part and/or the action can be determined according to the target known waveform.

By taking the first line in Table 1 as an example, suppose that the waveform of the target difference information is as shown by the waveform within the circle in FIG. 9, it can be obtained after computation that the similarity between the waveform of the target difference information and the known waveform A is the highest, the target known waveform can be determined as the known waveform A, and then it can be determined that the first part is an index finger and the action is single click.

Figure 24:
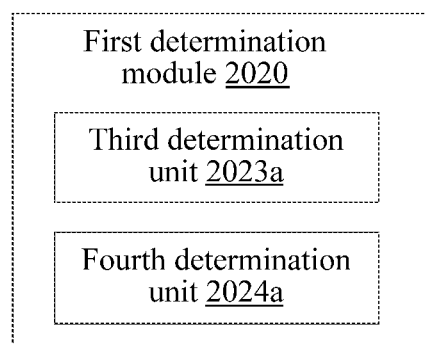
FIG. 24 is a module diagram of the first determination module in another implementation of the present application.

In addition, referring to FIG. 24, in another implementation, the first determination module 2020 comprises:

a third determination unit 2023*a*, configured to determine a signal feature of the target PPG information; and a fourth determination unit 2024*a*, configured to determine the first part and/or the action according to the signal feature and the reference information.

The signal feature of the target PPG information comprises at least one of a fingerprint, an average value and a difference of the target PPG information; the fingerprint consists of at least one of amplitude, phase and frequency spectrum of the target PPG information; the average value is an average value of at least one of the amplitude, the phase and the frequency spectrum of the target PPG information; the difference is a difference of at least one of the amplitude, the phase and the frequency spectrum of the target PPG information.

The reference information may be a reference signal feature obtained through pre-training, for example, in a training stage, it is feasible to execute a corresponding action according to Table 1 and correspondingly acquire a signal feature of the corresponding PPG information as the reference information. In specific applications, similarity between the signal feature of the target PPG information and a plurality of reference information can be computed, and a part and/or an action corresponding to the reference information with the highest similarity is taken as the first part and/or the action.

b) In another implementation, the target blood flow information is target Doppler measurement information, and correspondingly, the first determination module 2020 is configured to determine the first part and/or the action according to the target Doppler measurement information and reference information.

The target Doppler measurement information may be, for example, LDF (Laser Doppler Flowmetry), LDV (Laser Doppler Velocimety), ultrasonic Doppler shift and the like.

Figure 25:
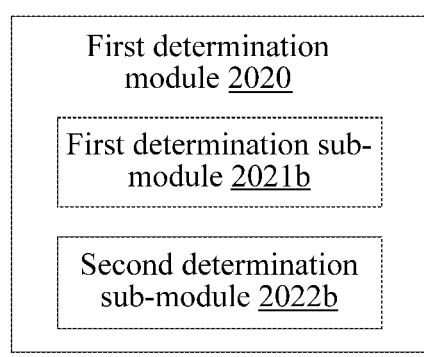
FIG. 25 is a module diagram of the first determination module in another implementation of the present application.

Referring to FIG. 25, in another implementation, the first determination module 2020 may comprise:

a first determination sub-module 2021*b*, configured to determine a signal feature of the target Doppler measurement information; and a second determination sub-module 2022*b*, configured to determine the first part and/or the action according to the signal feature and the reference information.

The signal feature of the target Doppler measurement information comprises at least one of a fingerprint, an average value and a difference of the target Doppler measurement information; the fingerprint consists of at least one of amplitude, phase and frequency spectrum of the target Doppler measurement information; the average value is an average value of at least one of the amplitude, the phase and the frequency spectrum of the target Doppler measurement information; the difference is a difference of at least one of the amplitude, the phase and the frequency spectrum of the target Doppler measurement information.

The reference information may be a reference signal feature obtained through pre-training, for example, in a training stage, it is feasible to execute a corresponding action according to Table 1 and correspondingly acquire a signal feature of the corresponding Doppler measurement information as the reference information. In specific applications, similarity between the signal feature of the target Doppler measurement information and a plurality of reference information can be computed, and a part and/or an action corresponding to the reference information with the highest similarity is taken as the first part and/or the action.

Figure 26:
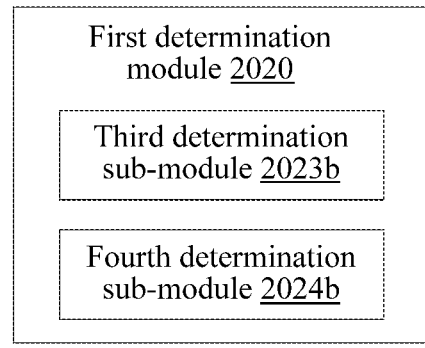
FIG. 26 is a module diagram of the first determination module in another implementation of the present application.

Referring to FIG. 26, in another implementation, the first determination module 2020 comprises:

a third determination sub-module 2023*b*, configured to determine target velocity related information corresponding to the target Doppler measurement information; and a fourth determination sub-module 2024*b*, configured to determine the first part and/or the action according to the target velocity related information and the reference information.

As stated above, the target Doppler measurement information may be, for example, LDF, LDV, ultrasonic Doppler shift and the like, which comprises a series of envelope wave signals, corresponding frequency-domain signals can be obtained by performing, for example, fast Fourier transform thereon, Doppler frequency components in the frequency-domain signals are in direct proportion to a blood flow velocity, a velocity of blood flow can be obtained, and blood flow can be determined further according to the blood flow velocity and the number of blood cells comprised in a blood cross section.

The data type of the target velocity related information may be the blood flow velocity, and may also be the flood flow. In other words, the target velocity related information may be target blood flow velocity information or target blood flow information. As the target Doppler measurement information comprises noise caused by the action, the target velocity related information also comprises the noise. Specifically, the noise comprises a change of the blood flow velocity caused by motion and/or a detection error caused by a change of contact between a detection device of the target Doppler measurement information and a limb (different actions will cause different changes of the contact between the detection device and the limb). In an ordinary LDF detection process, people generally tend to avoid such noise, but the present application achieves recognition of the action by use of such noise.

Figure 27:
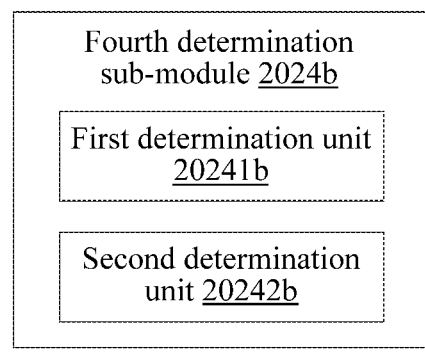
FIG. 27 is a module diagram of the fourth determination sub-module in one implementation of the present application.

In one implementation, referring to FIG. 27, the fourth determination sub-module 2024*b* may comprise:

a first determination unit 20241*b*, configured to determine target difference information according to the target velocity related information and the reference information; and a second determination unit 20242*b*, configured to determine the first part and/or the action at least according to the target difference information.

The reference information may have a different type. For example, in one implementation, the reference information is reference velocity related information corresponding to reference Doppler measurement information acquired by an acquisition part of the target Doppler measurement information in the event that the first part does not execute the action. Similar to the target velocity related information, the reference velocity related information may also be blood flow velocity or blood flow. In the event that the reference velocity related information is blood flow, a waveform thereof may be as shown in FIG. 14, it can be seen that it has an evident periodic regularity, and heart rate, pulse and other information can be obtained according to the waveform.

Figure 28:
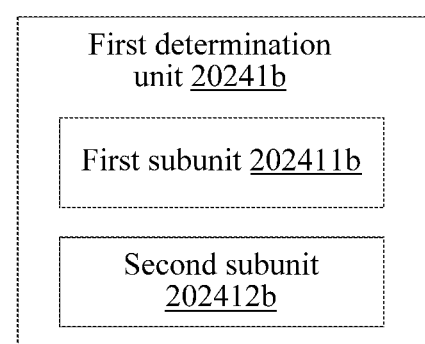
FIG. 28 is a module diagram of the first determination unit in one implementation of the present application.

Correspondingly, referring to FIG. 28, the first determination unit 20241*b* may comprise:

a first subunit 202411*b*, configured to divide the target velocity related information into a plurality of sub target velocity related information according to cycles; and a second subunit 202412*b*, configured to perform cross-correlation computation on the plurality of sub target velocity related information respectively with the reference information, and determine the target difference information according to a computation result.

In the event that an index finger executes a single click action, the waveform of the target velocity related information obtained is as shown in FIG. 15, and a total of 5 sub target velocity related information, C1, C2, C3, C4, and C5, can be obtained according to cycle division. The cycles are the same as those of the reference velocity related information.

The reference information may be, for example, a waveform between two crests in FIG. 14, after cross-correlation computation is performed on the reference information respectively with the 5 sub target velocity related information, it can be found that a cross-correlation computation result between the reference information and C3 is evidently less than that between the reference information and other sub target velocity related information, and it can be determined accordingly that sub target velocity related information corresponding to C3 is the target difference information.

In actual applications, it is feasible to compare the cross-correlation computation result between the reference information and each sub target velocity related information with a threshold, if the result is less than the threshold, it is considered that the corresponding sub target velocity related information is the target difference information. The threshold may be, for example, set as 80% of a cross-correlation computation result between the reference information and itself.

In another implementation, the reference information may be a first threshold, and the first threshold may be set according to an amplitude value of the reference velocity related information, for example, it is set as the minimum amplitude value or the maximum amplitude value of the reference velocity related information.

Correspondingly, the first determination unit 20241*b* is configured to compare an amplitude value in the target velocity related information with a value of the reference information, and determine the target difference information according to a comparison result.

By taking FIG. 16 as an example, which shows a waveform of the target velocity related information obtained in the event that the user's middle finger executes a single click action, the waveform within the circle is evidently distinguished from the waveform outside the circle, and the waveform within the circle is the waveform affected by the single click action, that is, the waveform corresponding to the target difference information. The reference information, for example, may be set as the minimum amplitude value of the reference velocity related information, for example, set as 450, then the amplitude value in the target velocity related information is compared with the amplitude value, it can be seen that the amplitude value of the waveform within the circle is less than the value of the reference information, and it can be determined that the target difference information is the waveform within the circle.

Those skilled in the art should understand that the two manners of determining the target difference information may also be used in combination, so as to increase accuracy and efficiency.

The second determination unit 20242*b* is configured to determine the first part and/or the action at least according to the target difference information.

Figure 29:
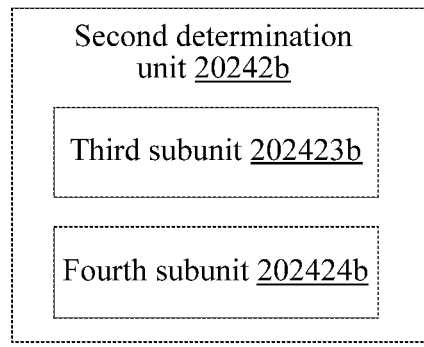
FIG. 29 is a module diagram of the second determination unit in one implementation of the present application.

In one implementation, referring to FIG. 29, the second determination unit 20242*b* comprises:

a third subunit 202423*b*, configured to compute similarity between a waveform of the target difference information and at least one known waveform, and determine a target known waveform according to a computation result; and a fourth subunit 202424*b*, configured to determine the first part and/or the action according to the target known waveform.

The at least one known waveform may be a set of multiple known waveforms, which can be obtained through pre-training, for example, a user orders the first part to execute different actions in advance and correspondingly acquire a waveform of the corresponding target difference information as the known waveform. So, a corresponding relationship between the first part, the action and the known waveform can be established, and the corresponding relationship can be as shown in Table 1.

In actual applications, similarity between the waveform of the target difference information and each known waveform in the set may be computed, and then a known waveform with the highest similarity is selected as the target known waveform. Then, the first part and/or the action can be determined according to the target known waveform.

By taking the first line in Table 1 as an example, suppose that the waveform of the target difference information is as shown by the waveform within the circle in FIG. 15, it can be obtained after computation that the similarity between the waveform of the target difference information and the known waveform A is the highest, the target known waveform can be determined as the known waveform A, and then it can be determined that the first part is an index finger and the action is single click.

In another implementation, the second determination unit 20242*b* is configured to determine the action according to the number of troughs or crests comprised in the target difference information.

The number of troughs or crests comprised in the target difference information is the same as the number of times the action is executed. As shown in FIG. 16, in the event of a single click action of a middle finger, the number of the corresponding troughs is 1; as shown in FIG. 15, in the event of a single click by an index finger, the number of the corresponding troughs or crests is 1. In addition, FIG. 17 is a waveform of target velocity related information obtained in the event of a double click by an index finger, a waveform within a circle corresponds to the target difference information, and it can be seen that, in this case, the number of the troughs or crests comprised in the target difference information is 2.

In another implementation, the second determination unit 20242*b* is configured to determine the action according to a cycle corresponding to the target difference information.

The cycle corresponding to the target difference information corresponds to a cycle within which the first part executes the action, in other words, the longer the time the first part executes the action each time is, the longer the cycle of the target difference information is. Therefore, the cycle corresponding to the target difference information may reflect a speed at which the action is executed, and then the action can be determined. For example, the first part is a foot, and if the cycle within which the foot executes a raise and lower action is 0.3 s, it can be determined that the corresponding action is walking; if the cycle within which the foot executes a raise and lower action is 0.03 s, it can be determined that the corresponding action is running. Certainly, in the event that the first part is a hand, whether the user is walking or running may also be determined according to a cycle of swinging back and forth of the hand.

Figure 30:
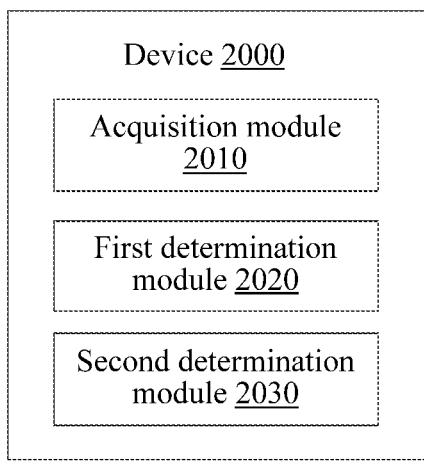
FIG. 30 is a module diagram of a device for determining an action and/or an action part in one implementation of the present application.

In one implementation, referring to FIG. 30, the device 2000 further comprises:

a second determination module 2030, configured to determine input information corresponding to the first part and/or the action.

A corresponding relationship between the first part and/or the action and the input information may be pre-determined, and the corresponding relationship may be as shown in Table 2. By taking the second line as an example, suppose that a smart bracelet is in communication with a smart glass, the smart bracelet acquires a user's action instruction and then controls the smart glass, and in the event that the smart bracelet recognizes a double click action of an index finger, the smart bracelet can control the smart glass to open an APP currently presented to the user, for example, open a photograph function. The relationship table shown in Table 2 can be pre-stored in, for example, the smart bracelet and other wearable devices, and such a relationship table can be given in an operation instruction thereof, so as to teach and train the user to execute corresponding command input through an action similar to that in Table 2.

One application scenario of the method and device for determining input information according to the embodiment of the present application may be as follows: a user wears a smart bracelet on a left wrist part, when the user wants to know the current time, the user uses a right index finger to quickly click twice near the left wrist (for example, one side of the wrist close to the shoulder), the bracelet, by detecting changes of PPG information of the left wrist, recognizes that the user presses twice briefly, and determines that corresponding input information is a display time command, then the command is input for a control module, and the control module controls the bracelet to output the current time through voice or the like; when the user wants to make the bracelet dormant, the user uses the right index finger to press near the left wrist for a period of time, the bracelet, by detecting changes of PPG information of the left wrist, recognizes that the user presses continuously over 3 s, and determines that the corresponding input information is a dormant command, then the command is input for the control module, and the control module controls the bracelet to enter a dormant mode.

Figure 31:
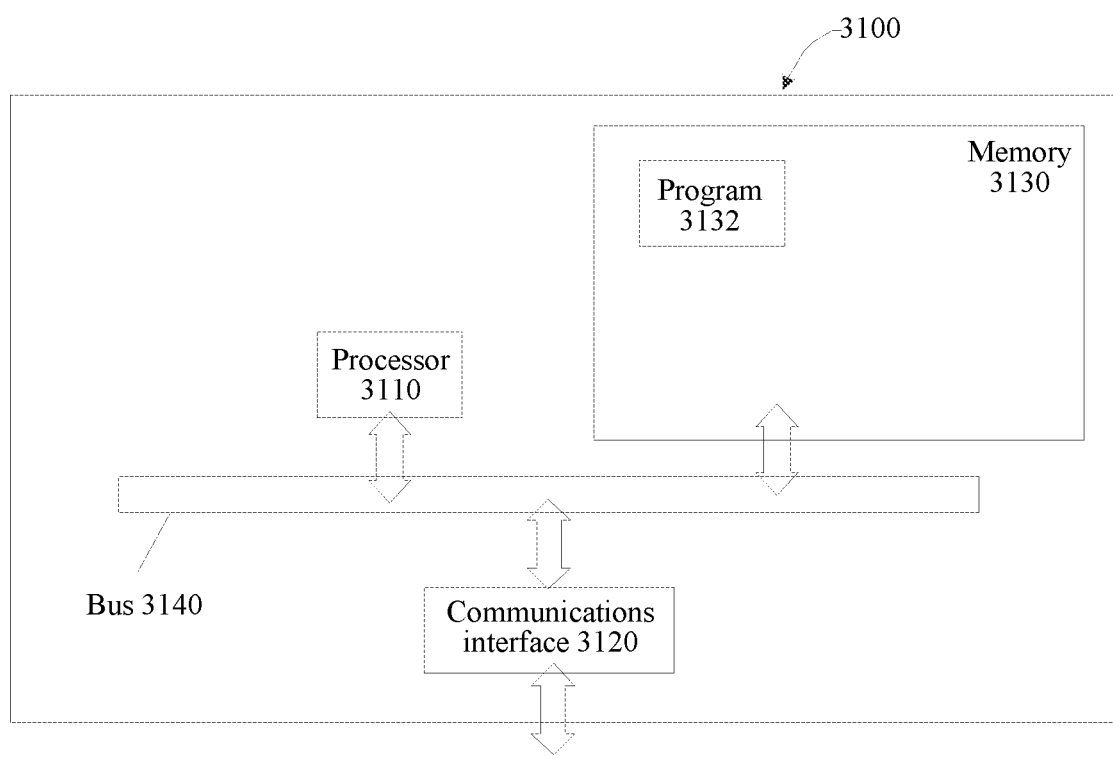
FIG. 31 is a schematic diagram of a hardware structure of the device for determining an action and/or an action part in one implementation of the present application.

A hardware structure of the device for determining an action and/or an action part according to another embodiment of the present application is as shown in FIG. 31. The specific embodiment of the present application does not limit the specific implementation of the device for determining an action and/or an action part; referring to FIG. 31, the device 3100 may comprise:

a processor 3110, a Communications Interface 3120, a memory 3130, and a communications bus 3140.

The processor 3110, the Communications Interface 3120, and the memory 3130 accomplish mutual communications via the communications bus 3140.

The Communications Interface 3120 is configured to communicate with other network elements.

The processor 3110 is configured to execute a program 3132, and specifically, can implement relevant steps in the method embodiment shown in FIG. 1.

For example, the program 3132 may comprise a program code, the program code comprising computer operation instructions.

The processor 3110 may be a central processing unit (CPU), or an application specific integrated circuit (ASIC), or be configured to be one or more integrated circuits which implement the embodiments of the present application.

The memory 3130 is configured to store the program 3132. The memory 3130 may comprise a high-speed Random Access Memory (RAM) memory, and may also comprise a non-volatile memory, for example, at least one magnetic disk memory. The program 3132 may specifically perform the following steps:

in response to that a first part on a body of a user executes an action, acquiring target blood flow information of the first part or a second part corresponding to the first part; and determining the first part and/or the action according to the target blood flow information and reference information.

Reference can be made to corresponding description in the corresponding steps or modules in the embodiments for specific implementation of the steps in the program 3132, which is not repeated herein. Those skilled in the art can clearly understand that, reference can be made to the corresponding process description in the method embodiments for the specific working procedures of the devices and the modules described above, and will not be repeated herein in order to make the description convenient and concise.

It can be appreciated by those of ordinary skill in the art that each exemplary unit and method step described with reference to the embodiments disclosed herein can be implemented by electronic hardware or a combination of computer software and electronic hardware. Whether these functions are executed in a hardware mode or a software mode depends on particular applications and design constraint conditions of the technical solution. The professional technicians can use different methods to implement the functions described with respect to a particular application, but such implementation should not be considered to go beyond the scope of the present application.

If the functions are implemented in the form of a software functional unit and is sold or used as an independent product, it can be stored in a non-transitory computer-readable storage medium. Based on such understanding, the technical solution of the present application essentially or the part which contributes to the prior art or a part of the technical solution can be embodied in the form of a software product, and the computer software product is stored in a storage medium, and comprises several instructions for enabling a computer device (which can be a personal computer, a server, or a network device, and the like) to execute all or some steps of the method described in each embodiment of the present application. The foregoing storage medium comprises, a USB disk, a removable hard disk, a read-only memory (ROM), a random access memory (RAM), a magnetic disk, an optical disk or any other mediums that can store program codes.

The above implementations are only intended to describe the present application rather than to limit the present application; various changes and variations can be made by those of ordinary skill in the art without departing from the spirit and scope of the present application, so all equivalent technical solutions also belong to the scope of the present application, and the scope of patent protection of the present application should be defined by the claims.

What is claimed is:

1. A method for determining an action and an action part, comprising:
   in response to detecting a motion of a first part of a body of a user, acquiring, using a photoelectric sensor, target Doppler measurement information of the first part or a second part corresponding to the first part;
   determining target velocity related information corresponding to the target Doppler measurement information; and
   determining the first part and the action according to the target velocity related information and reference information,
   wherein the target velocity related information comprises target blood flow velocity information or target blood flow information.

2. The method of claim 1, wherein the determining the first part and the action according to the target velocity related information and the reference information comprises:
   determining target difference information according to the target velocity related information and the reference information; and
   determining the first part and the action at least according to the target difference information.

3. The method of claim 2, wherein the determining target difference information according to the target velocity related information and the reference information comprises:
   dividing the target velocity related information into a plurality of sub target velocity related information according to cycles; and
   performing cross-correlation computation on the plurality of sub target velocity related information respectively with the reference information, and determining the target difference information according to a computation result.

4. The method of claim 2, wherein the reference information is reference velocity related information corresponding to reference Doppler measurement information acquired in an acquisition part of the target Doppler measurement information in the event that the first part does not execute the action.

5. The method of claim 2, wherein the determining target difference information according to the target velocity related information and the reference information comprises:
   comparing an amplitude value in the target velocity related information with a value of the reference information, and determining the target difference information according to a comparison result.

6. The method of claim 5, wherein the reference information is a first threshold.

7. The method of claim 2, wherein the determining the first part and the action at least according to the target difference information comprises:
   computing similarity between a waveform of the target difference information and at least one known waveform, and determining a target known waveform according to a computation result; and
   determining the first part and the action according to the target known waveform.

8. The method of claim 2, wherein the determining the first part and the action at least according to the target difference information comprises:
   determining the action according to the number of troughs or crests comprised in the target difference information.

9. The method of claim 2, wherein the determining the first part and the action at least according to the target difference information comprises:
   determining the action according to a cycle corresponding to the target difference information.

10. The method of claim 1, wherein the method further comprises:
    determining input information corresponding to the first part and the action.

11. The method of claim 1, wherein the first part is a hand or wrist of the user.

12. A device for determining an action and an action part, comprising:
    an acquisition module, configured to, in response to detecting a motion of a first part of a body of a user, acquire, using a photoelectric sensor, target Doppler measurement information of the first part or a second part corresponding to the first part; and
    a first determination module, configured to determine the first part and the action by:
       determining target velocity related information corresponding to the target Doppler measurement information; and
       determining the first part and the action according to the target velocity related information and reference information,
       wherein the target velocity related information comprises target blood flow velocity information or target blood flow information.

13. A method for determining an action and an action part, comprising:
    in response to detecting a motion of a first part of a body of a user, acquiring, using a photoelectric sensor, target blood flow information of the first part or a second part corresponding to the first part, wherein the target blood flow information comprises target Doppler measurement information;
    determining target velocity related information corresponding to the target Doppler measurement information; and
    determining the first part and the action according to the target velocity related information and reference information,
    wherein the target velocity related information comprises target blood flow velocity information.

14. A device for determining an action and an action part, comprising:
    an acquisition module, configured to, in response to detecting a motion of a first part of a body of a user, acquire, using a photoelectric sensor, target blood flow information of the first part or a second part corresponding to the first part, wherein the target blood flow information comprises target Doppler measurement information; and
    a first determination module, configured to determine the first part and the action by:
       determining target velocity related information corresponding to the target Doppler measurement information; and
       determine the first part and the action according to the target velocity related information and reference information;
       wherein the target velocity related information comprises target blood flow velocity information.

15. A device for determining an action and an action part, the device comprising a processor and a memory, the memory storing computer executable instructions that, when executed by the processor, cause the device to perform operations comprising:

in response to detecting a motion of a first part of a body of a user, acquiring, using a photoelectric sensor, target Doppler measurement information of the first part or a second part corresponding to the first part;

determining target velocity related information corresponding to the target Doppler measurement information; and determining the first part and the action according to the target velocity related information and reference information, wherein the target velocity related information comprises target blood flow velocity information or target blood flow information.

16. The device of claim 15, wherein the operations further comprise:

determining target difference information according to the target velocity related information and the reference information; and determining the first part and the action at least according to the target difference information.

17. The device of claim 16, wherein the operations further comprise:

dividing the target velocity related information into a plurality of sub target velocity related information according to cycles; and performing cross-correlation computation on the plurality of sub target velocity related information respectively with the reference information, and determining the target difference information according to a computation result.

18. The device of claim 16, wherein the operations further comprise:

comparing an amplitude value in the target velocity related information with a value of the reference information, and determining the target difference information according to a comparison result.

19. The device of claim 16, wherein the operations further comprise:

computing similarity between a waveform of the target difference information and at least one known waveform, and determining a target known waveform according to a computation result; and determining the first part and the action according to the target known waveform.

20. The device of claim 16, wherein the operations further comprise: determining the action according to the number of troughs or crests comprised in the target difference information.

21. The device of claim 16, wherein the operations further comprise: determining the action according to a cycle corresponding to the target difference information.

22. The device of claim 15, wherein the operations further comprise: determining input information corresponding to the first part and the action.

23. A wearable device, wherein the wearable device comprises the device for determining an action and an action part of claim 15.

24. A non-transitory computer readable medium, comprising at least one executable instruction, which, in response to execution, causes a processor to perform operations comprising:

in response to detecting a motion of a first part of a body of a user, acquiring, using a photoelectric sensor, target Doppler measurement information of the first part or a second part corresponding to the first part;

determining target velocity related information corresponding to the target Doppler measurement information; and determining the first part and an action according to the target velocity related information and reference information, wherein the target velocity related information comprises target blood flow velocity information or target blood flow information.

25. A device for determining an action and an action part, the device comprising a processor and a memory, the memory storing computer executable instructions that, when executed by the processor, cause the device to perform operations comprising:

in response to detecting a motion of a first part of a body of a user, acquiring, using a photoelectric sensor, target blood flow information of the first part or a second part corresponding to the first part, wherein the target blood flow information comprises target Doppler measurement information;

determining target velocity related information corresponding to the target Doppler measurement information; and determining the first part and the action according to the target velocity related information and reference information, wherein the target velocity related information comprises target blood flow velocity information.

26. A non-transitory computer readable medium, comprising at least one executable instruction, which, in response to execution, causes a processor to perform operations comprising:

in response to detecting a motion of a first part of a body of a user, acquiring, using a photoelectric sensor, target blood flow information of the first part or a second part corresponding to the first part, wherein the target blood flow information comprises target Doppler measurement information;

determining target velocity related information corresponding to the target Doppler measurement information; and determining the first part and an action according to the target velocity related information and reference information, wherein the target velocity related information comprises target blood flow velocity information.

* * * * *